United States Patent
Zones et al.

(10) Patent No.: US 12,420,270 B2
(45) Date of Patent: Sep. 23, 2025

(54) MOLECULAR SIEVE SSZ-116, ITS SYNTHESIS AND USE

(71) Applicant: CHEVRON U.S.A. INC., San Ramon, CA (US)

(72) Inventors: Stacey Ian Zones, San Francisco, CA (US); Jesus Pascual, Berkeley, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 479 days.

(21) Appl. No.: 18/064,324

(22) Filed: Dec. 12, 2022

(65) Prior Publication Data
US 2023/0130060 A1    Apr. 27, 2023

Related U.S. Application Data

(62) Division of application No. 17/023,709, filed on Sep. 17, 2020, now Pat. No. 11,571,685.

(60) Provisional application No. 62/962,032, filed on Jan. 16, 2020.

(51) Int. Cl.
| | |
|---|---|
| *C07D 233/58* | (2006.01) |
| *B01J 29/04* | (2006.01) |
| *B01J 29/70* | (2006.01) |
| *B01J 37/00* | (2006.01) |
| *B01J 37/04* | (2006.01) |
| *B01J 37/10* | (2006.01) |
| *C01B 39/02* | (2006.01) |
| *C01B 39/06* | (2006.01) |
| *C01B 39/48* | (2006.01) |
| *C07C 4/06* | (2006.01) |

(52) U.S. Cl.
CPC ............. *B01J 29/047* (2013.01); *B01J 29/70* (2013.01); *B01J 37/0018* (2013.01); *B01J 37/04* (2013.01); *B01J 37/10* (2013.01); *C01B 39/026* (2013.01); *C01B 39/06* (2013.01); *C01B 39/065* (2013.01); *C01B 39/48* (2013.01); *C07C 4/06* (2013.01); *C07D 233/58* (2013.01); *C01P 2002/72* (2013.01); *C01P 2002/78* (2013.01); *C01P 2004/03* (2013.01); *C07C 2529/04* (2013.01)

(58) Field of Classification Search
CPC .................................................... C07D 233/58
See application file for complete search history.

(56) References Cited

U.S. PATENT DOCUMENTS

2008/0032994 A1* 2/2008 Borgers ............... C07D 405/10
544/371

OTHER PUBLICATIONS

No new references cited by the Examiner.*

* cited by examiner

*Primary Examiner* — Shawquia Jackson

(57) ABSTRACT

A novel synthetic crystalline aluminogermanosilicate molecular sieve material, designated SSZ-116, is provided. SSZ-116 can be synthesized using 3-[(3,5-di-tert-butylphenyl)methyl]-1,2-dimethyl-1H-imidazolium cations as a structure directing agent. SSZ-116 may be used in organic compound conversion reactions and/or sorptive processes. This disclosure also relates to the structure directing agents used in the methods for making the SSZ-116 material as well as the synthesis method used to prepare such structure directing agents.

1 Claim, No Drawings

MOLECULAR SIEVE SSZ-116, ITS SYNTHESIS AND USE

CROSS-REFERENCE TO RELATED APPLICATIONS

This application is a divisional application of U.S. patent application Ser. No. 17/023,709, filed Sep. 17, 2020, which claims priority to and the benefit of U.S. Provisional Patent Application No. 62/962,032, filed Jan. 16, 2020, the disclosures of which are incorporated herein by reference in their entirety.

FIELD

This disclosure relates to a novel synthetic crystalline molecular sieve designated SSZ-116, its synthesis, and its use in organic compound conversion reactions and sorption processes.

BACKGROUND

Molecular sieves are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve.

According to the present disclosure, a new crystalline molecular sieve, designated SSZ-116 and having a unique powder X-ray diffraction pattern, has been synthesized using 3-[(3,5-di-tert-butylphenyl)methyl]-1,2-dimethyl-1H-imidazolium cations as a structure directing agent.

SUMMARY

In a first aspect, there is provided a molecular sieve having, in its as-synthesized form, a powder X-ray diffraction pattern including at least the peaks in Table 3 below.

In its as-synthesized and anhydrous form, the molecular sieve can have a chemical composition comprising the following molar relationship:

|  | Broadest | Secondary |
|---|---|---|
| $TO_2/Al_2O_3$ | ≥30 | ≥50 |
| $Q/TO_2$ | >0 to 0.1 | >0 to 0.1 | wherein T is a tetravalent element comprising silicon and germanium; and Q comprises 3-[(3,5-di-tert-butylphenyl) methyl]-1,2-dimethyl-1H-imidazolium cations.

In a second aspect, there is provided a molecular sieve having, in its calcined form, a powder X-ray diffraction pattern including at least the peaks in Table 4 below.

In its calcined form, the molecular sieve can have a chemical composition comprising the following molar relationship:

$Al_2O_3$:(n)$TO_2$

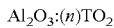

wherein n is ≥30; and T is a tetravalent element comprising silicon and germanium.

In a third aspect, there is provided a method of synthesizing the molecular sieve described herein, the method comprising (a) providing a reaction mixture comprising: (1) a FAU framework type zeolite; (2) a source of germanium; (3) a structure directing agent comprising 3-[(3,5-di-tert-butylphenyl)methyl]-1,2-dimethyl-1H-imidazolium cations (Q); (4) a source of fluoride ions; and (5) water; and (b) subjecting the reaction mixture to crystallization conditions sufficient to form crystals of the molecular sieve.

In a fourth aspect, there is provided a process of converting a feedstock comprising an organic compound to a conversion product which comprises contacting the feedstock at organic compound conversion conditions with a catalyst comprising the molecular sieve described herein.

In a fifth aspect, there is provided an organic nitrogen compound comprising a cation having the following structure:

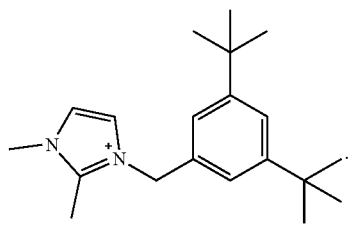 [SMILES: Cc1n(C)cc[n+]1Cc1cc(C(C)(C)C)cc(C(C)(C)C)c1]

DETAILED DESCRIPTION

Definitions

The term "framework type" has the meaning described in the "*Atlas of Zeolite Framework Types,*" by Ch. Baerlocher and L. B. McCusker and D. H. Olsen (Elsevier, Sixth Revised Edition, 2007).

The term "zeolite" refers a synthetic aluminosilicate molecular sieve having a framework constructed of alumina and silica (i.e., repeating $SiO_4$ and $AlO_4$ tetrahedral units).

The term "aluminogermanosilicate" refers to a crystalline microporous solid including aluminum, germanium and silicon oxides within its framework structure. The aluminogermanosilicate may be a "pure-aluminogermanosilicate" (i.e., absent other detectable metal oxides with its framework structure) or optionally substituted. When described as "optionally substituted," the respective framework may contain other atoms (e.g., B, Ga, In, Fe, Ti, Zr) substituted for one or more of the atoms not already present in the parent framework.

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

As used herein, the numbering scheme for the Periodic Table Groups is as disclosed in *Chem. Eng. News* 1985, 63(5), 26-27.

Synthesis of the Molecular Sieve

Molecular sieve SSZ-116 may be synthesized by: (a) providing a reaction mixture comprising (1) a FAU framework type zeolite; (2) a source of germanium; (3) a structure directing agent comprising 3-[(3,5-di-tert-butylphenyl) methyl]-1,2-dimethyl-1H-imidazolium cations (Q); (4) a source of fluoride ions; and (5) water; and (b) subjecting the reaction mixture to crystallization conditions sufficient to form crystals of the molecular sieve.

The reaction mixture can have a composition, in terms of molar ratios, within the ranges set forth in Table 1:

TABLE 1

| Reactants | Broadest | Secondary |
| --- | --- | --- |
| TO$_2$/Al$_2$O$_3$ | 30 to 600 | 60 to 500 |
| Q/TO$_2$ | 0.10 to 1.00 | 0.20 to 0.70 |
| F/TO$_2$ | 0.10 to 1.00 | 0.20 to 0.70 |
| H$_2$O/TO$_2$ | 2 to 10 | 4 to 8 | wherein T is a tetravalent element comprising silicon and germanium; and Q comprises 3-[(3,5-di-tert-butylphenyl) methyl]-1,2-dimethyl-1H-imidazolium cations.

The FAU framework type zeolite can be the only silica and aluminum source. The FAU framework type zeolite can be zeolite Y. The FAU framework type zeolite can comprise two or more zeolites. The two or more zeolites can be Y zeolites having different silica-to-alumina molar ratios.

Suitable sources of germanium include germanium dioxide and germanium alkoxides (e.g., tetraethoxygermanium, tetraisopropoxygermanium).

The reaction mixture may have a molar ratio of SiO$_2$/GeO$_2$ in a range of from 4 to 12 (e.g., 6 to 10).

Suitable sources of fluoride ions include hydrogen fluoride, ammonium fluoride, and ammonium bifluoride.

SSZ-116 is synthesized using a structure directing agent comprising 3-[(3,5-di-tert-butylphenyl)methyl]-1,2-dimethyl-1H-imidazolium cations (Q), represented by the following structure (1):

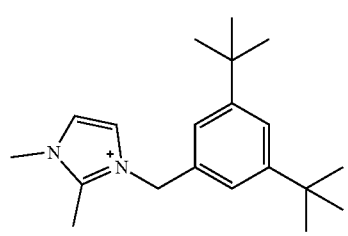

(1)

Suitable sources of Q are the hydroxides and/or other salts of the quaternary ammonium compound.

The reaction mixture may have a molar ratio of Q/F in a range of from 0.80 to 1.20 (e.g., 0.85 to 1.15, 0.90 to 1.10, 0.95 to 1.05, or 1 to 1).

The reaction mixture may contain seeds of a molecular sieve material, such as SSZ-116 from a previous synthesis, in an amount of from 0.01 to 10,000 ppm by weight (e.g., 100 to 5000 ppm by weight) of the reaction mixture. Seeding can be advantageous in decreasing the amount of time necessary for complete crystallization to occur. In addition, seeding can lead to an increased purity of the product obtained by promoting the nucleation and/or formation of SSZ-116 over any undesired phases.

It is noted that the reaction mixture components can be supplied by more than one source. Also, two or more reaction components can be provided by one source. The reaction mixture can be prepared either batchwise or continuously.

Crystallization and Post-Synthesis Treatment

Crystallization of the molecular sieve from the above reaction mixture can be carried out under either static, tumbled or stirred conditions in a suitable reactor vessel (e.g., a polypropylene jar or a Teflon-lined or stainless-steel autoclave) placed in a convection oven at a temperature of from 125° C. to 200° C. for a time sufficient for crystallization to occur at the temperature used (e.g., 1 day to 14 days). The hydrothermal crystallization process is typically conducted under pressure, such as in an autoclave, and is preferably under autogenous pressure.

Once the molecular sieve crystals have formed, the solid product is separated from the reaction mixture by standard separation techniques such as centrifugation or filtration. The recovered crystals are water-washed and then dried, for several seconds to a few minutes (e.g., 5 seconds to 10 minutes for flash drying) or several hours (e.g., about 4 to 24 hours for oven drying at 75° C. to 150° C.), to obtain as-synthesized molecular sieve crystals. The drying step can be performed at atmospheric pressure or under vacuum.

As a result of the crystallization process, the recovered crystalline molecular sieve product contains within its pore structure at least a portion of the structure directing agent used in the synthesis.

The as-synthesized molecular sieve may be subjected to treatment to remove part or all of the structure directing agent used in its synthesis. This is conveniently effected by thermal treatment (e.g., calcination) in which the as-synthesized molecular sieve is heated at a temperature sufficient to remove part or all of the structure directing agent. The thermal treatment may be carried out in any manner conventionally known in the art. Suitable conditions include heating at a temperature of at least 300° C. (e.g., at least about 370° C.) for at least 1 minute and generally not longer than 20 hours, for example, for a period of from 1 hour to 12 hours. While sub-atmospheric pressure can be employed for the thermal treatment, atmospheric pressure is desired for reasons of convenience. The thermal treatment can be performed at a temperature up to about 925° C. For instance, the thermal treatment can be conducted at a temperature of from 400° C. to 600° C. in the presence of an oxygen-containing gas.

Any extra-framework cations in the molecular sieve can be replaced in accordance with techniques well known in the art (e.g., by ion exchange) with hydrogen, ammonium, or any desired metal cation.

Characterization of the Molecular Sieve

In its as-synthesized and anhydrous form, molecular sieve SSZ-116 can have a chemical composition comprising the following molar relationship set forth in Table 2:

TABLE 2

| | Broadest | Secondary |
| --- | --- | --- |
| TO$_2$/Al$_2$O$_3$ | ≥30 | ≥50 |
| Q/TO$_2$ | >0 to 0.1 | >0 to 0.1 | wherein T is a tetravalent element comprising silicon and germanium; and Q comprises 3-[(3,5-di-tert-butylphenyl) methyl]-1,2-dimethyl-1H-imidazolium cations. In some aspects, the molecular sieve can have a SiO$_2$/GeO$_2$ molar ratio in a range of 4 to 12 (e.g., 6 to 10).

In its calcined form, molecular sieve SSZ-116 can have a chemical composition comprising the following molar relationship:

Al$_2$O$_3$:(n)TO$_2$ wherein n is ≥30 (e.g., 30 to 500, ≥50, 50 to 250, or 50 to 150); and T is a tetravalent element comprising silicon and germanium.

Molecular sieve SSZ-116 is characterized by a powder XRD pattern, which, in the as-synthesized form of the molecular sieve, includes at least the peaks set forth in Table 3, and which, in the calcined form of the molecular sieve, includes at least the peaks set forth in Table 4.

TABLE 3

Characteristic Peaks for As-Synthesized SSZ-116

| 2-Theta[a] [°] | d-Spacing [Å] | Relative Intensity |
|---|---|---|
| 8.59 | 10.29 | m |
| 11.11 | 7.96 | w |
| 15.65 | 5.66 | vs |
| 17.49 | 5.07 | w |
| 20.87 | 4.25 | m |
| 23.02 | 3.86 | m |
| 23.60 | 3.77 | w |
| 24.05 | 3.70 | w |
| 25.30 | 3.52 | m |
| 25.90 | 3.44 | m |
| 26.91 | 3.31 | w |

[a] ±0.30

TABLE 4

Characteristic Peaks for Calcined SSZ-116

| 2-Theta[a] [°] | d-Spacing [Å] | Relative Intensity |
|---|---|---|
| 8.68 | 10.18 | vs |
| 11.23 | 7.87 | w |
| 15.60 | 5.68 | vs |
| 17.68 | 5.01 | vs |
| 20.79 | 4.27 | m |
| 23.14 | 3.84 | w |
| 23.56 | 3.77 | w |
| 23.98 | 3.71 | w |
| 25.20 | 3.53 | w |
| 25.83 | 3.42 | vs |
| 26.83 | 3.32 | w |

[b] ±0.30

The powder X-ray diffraction patterns presented herein were collected by standard techniques. The radiation was CuKα radiation. The interplanar spacings, d-spacings, were calculated in Angstrom units, and the relative intensities of the lines, $I/I_o$, represents the ratio of the peak intensity to the intensity of the strongest line, above background. The intensities are uncorrected for Lorentz and polarization effects. The relative intensities are given in terms of the following notations: w (weak) is <20; m (medium) is ≥20 to <40; s (strong) is ≥40 to <60; and vs (very strong) is ≥60.

Minor variations in the diffraction pattern can result from variations in the mole ratios of the framework species of the sample due to changes in lattice constants. In addition, disordered materials and/or sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

Sorption and Catalysis

Molecular sieve SSZ-116 (where part or all of the structure directing agent is removed) may be used as a sorbent or as a catalyst to catalyze a wide variety of organic compound conversion processes including many of present commercial/industrial importance. Examples of chemical conversion processes which are effectively catalyzed by SSZ-116, by itself or in combination with one or more other catalytically active substances including other crystalline catalysts, include those requiring a catalyst with acid activity. Examples of organic conversion processes which may be catalyzed by SSZ-116 include cracking, hydrocracking, disproportionation, alkylation, oligomerization, aromatization, and isomerization.

As in the case of many catalysts, it may be desirable to incorporate SSZ-116 with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring, or in the form of gelatinous precipitates or gels, including mixtures of silica and metal oxides. Use of a material in conjunction with SSZ-116 (i.e., combined therewith or present during synthesis of the new material) which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with SSZ-116 include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with SSZ-116 also include inorganic oxides, such as silica, zirconia, titania, magnesia, beryllia, alumina, and mixtures thereof.

In addition to the foregoing materials, SSZ-116 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of SSZ-116 and inorganic oxide matrix may vary widely, with the SSZ-116 content ranging from 1 to 90 wt. % (e.g., 2 to 80 wt. %) of the composite.

EXAMPLES

The following illustrative examples are intended to be non-limiting.

Example 1

Synthesis of 3-[(3,5-di-tert-butylphenyl)methyl]-1,2-dimethyl-1H-imidazolium hydroxide A 100 mL round bottom flask equipped with a magnetic stir bar was charged with 8 g of 3,5-di-tert-butylbenzyl bromide, 2.99 g of 1,2-dimethylimidazole and 60 mL of toluene. A reflux condenser was then attached, and the mixture heated at 96° C. for 24 hours. After cooling, the mixture was filtered, and the solid residue was washed with ethyl acetate. The solids were then dried under vacuum.

The resulting bromide salt was exchanged to the corresponding hydroxide salt by stirring it with hydroxide exchange resin in deionized water overnight. The solution was filtered, and the filtrate was analyzed for hydroxide concentration by titration of a small sample with a standard solution of 0.1 N HCl.

Example 2

Synthesis of SSZ-116

Into a tared 23 mL Parr reactor was added 0.27 g of Tosoh 390HUA Y-zeolite ($SiO_2/Al_2O_3$ molar ratio ~300), 0.05 g of $GeO_2$ and 2.5 mmoles of an aqueous 3-[(3,5-di-tert-butylphenyl)methyl]-1,2-dimethyl-1H-imidazolium hydroxide solution. The reactor was then placed in a vented hood and water was allowed to evaporate to bring the $H_2O/(SiO_2+GeO_2)$ molar ratio to 7 (as determined by the total mass of the suspension). Then, HF (2.5 mmoles) was added and the reactor was heated to 160° C. with tumbling at 43 rpm for about 7 days. The solid products were recovered by centrifugation, washed with deionized water and dried at 95° C.

Powder XRD showed the product to be a pure form of a new phase, SSZ-116.

The product had a $SiO_2/GeO_2$ molar ratio of 8.

Example 3

Calcination of SSZ-116

The as-synthesized molecular sieve of Example 1 was calcined inside a muffle furnace under a flow of air at 550° C. for 5 hours, then cooled and analyzed by powder XRD.

The powder XRD pattern of the calcined material indicated that the material remains stable after calcination to remove the structure directing agent.

Example 4

Micropore Volume Analysis

Analysis of the calcined form of SSZ-116 by the t-plot method of nitrogen physisorption shows the sample possesses 38.00 m²/g external surface area and 0.1178 cm³/g micropore volume. All $N_2$ adsorption isotherms were performed at 77 K with a TriStar II instrument (Micromeritics). Prior to analysis, the samples were outgassed under vacuum at 400° C. The t-plot method was used to calculate the micropore volumes on the adsorption branch.

Analysis of the hydrogen form of SSZ-116 by the t-plot method of argon physisorption shows the sample possesses 51.552 m²/g external surface area and 0.058 cm³/g micropore volume. Argon physisorption was conducted on a Quantachrome Autosorb iQ instrument. Prior to adsorption measurements, samples were outgassed by heating (at a rate of 10° C./min) the sample under vacuum for 1 hour at 80° C., 3 hours at 120° C. and 10 hours at 350° C. Adsorption isotherms were collected using argon at 87.45 K using the constant dose (quasi-equilibrium) method. Micropore volumes were obtained from the adsorption branch of the isotherms using the t-plot method (0.1<$P/P_0$<0.3).

Example 5

Constraint Index Testing

Constraint Index (CI) is a test describing the relative propensity of a material to crack linear alkanes versus branched alkanes. The competitive cracking of n-hexane versus 3-methylpentane was first described by W. O. Haag et al. (*J. Catal.* 1981, 67, 218-222). Additional work to help clarify results of the test have been performed by S. I. Zones et al. (*Micropor. Mesopor. Mater.* 2000, 35-36, 31-46) and M. E. Davis et al. (*J. Catal.* 2010, 269, 64-70). The CI value may be calculated using Equation 1 (X denotes the fractional conversion of each species) and thus it is proportional to the observed cracking rate constants of n-hexane ($nC_6$) to 3-methylpentane (3MP).

$$CI = \frac{\log(1 - X_{nC6})}{\log(1 - X_{3MP})} \quad \text{(Equation 1)}$$

As is typically reported, small pore zeolites usually exhibit CI values greater than 12; medium pore zeolites often exhibit CI values in a range of from 2 to 12; and large pore zeolites usually exhibit CI values of less than 1.

The hydrogen form of SSZ-116 prepared per Example 4 was pelletized at 4 kpsi, crushed and granulated to 20-40 mesh. A 0.6 g sample of the granulated material was calcined in air at 540° C. for 4 hours and cooled in a desiccator to ensure dryness. Then, 0.47 g of material was packed into a ¼ inch stainless steel tube with alundum on both sides of the molecular sieve bed. A furnace (Applied Test Systems, Inc.) was used to heat the reactor tube. Nitrogen was introduced into the reactor tube at 9.4 mL/min and at atmospheric pressure. The reactor was heated to about 800° F. (427° C.), and a 50/50 feed of n-hexane and 3-methylpentane (3MP) was introduced into the reactor at a rate of 8 µL/min. The feed was delivered by an ISCO pump. Direct sampling into a GC began after 15 minutes of feed introduction. Test data results after 15 minutes on stream (800° F.) are presented in Table 5.

TABLE 5

| Constraint Index Test | |
|---|---|
| n-Hexane Conversion, % | 0.2 |
| 3-Methylpentane Conversion, % | 0.6 |
| Feed Conversion, % | 0.4 |
| Constraint Index (excluding 2MP) | 0.35 |
| Constraint Index (including 2MP) | 0.36 |

Example 6

Example 2 was repeated except that CBV-780 Y-zeolite ($SiO_2/Al_2O_3$ molar ratio=80; Zeolyst International) was used as the FAU source. Powder XRD showed the product to be SSZ-116.

Example 7

Example 2 was repeated except that CBV-760 Y-zeolite ($SiO_2/Al_2O_3$ molar ratio=60; Zeolyst International) was used as the FAU source. Powder XRD showed the product to be SSZ-116.

Elemental analysis showed that the product had a silicon content of 14.7 wt. %, a germanium content of 4.8 wt. %, an aluminum content of 0.34 wt. %, a Si/Ge molar ratio of 7.66, and a $(SiO_2+GeO_2)/Al_2O_3$ molar ratio of 95.

Example 8

Example 2 was repeated except that CBV-720 Y-zeolite ($SiO_2/Al_2O_3$ molar ratio=30; Zeolyst International) was used as the FAU source. Powder XRD showed the product to be SSZ-116. As-synthesized SSZ-116 was calcined as described in Example 3.

Analysis of calcined SSZ-116 by the t-plot method of nitrogen physisorption shows the sample possessed a micropore volume of 0.11 cm³/g.

Example 9

Brønsted Acidity

Brønsted acidity of the molecular sieve of Example 8 in its calcined form was determined by n-propylamine temperature-programmed desorption (TPD) adapted from the published descriptions by T. J. Gricus Kofke et al. (J. Catal. 1988, 114, 34-45); T. J. Gricus Kofke et al. (J. Catal. 1989, 115, 265-272); and J. G. Tittensor et al. (J. Catal. 1992, 138, 714-720). A sample was pre-treated at 400° C.-500° C. for 1 hour in flowing dry $H_2$. The dehydrated sample was then cooled down to 120° C. in flowing dry helium and held at 120° C. for 30 minutes in a flowing helium saturated with n-propylamine for adsorption. The n-propylamine-saturated sample was then heated up to 500° C. at a rate of 10° C./minute in flowing dry helium. The Brønsted acidity was calculated based on the weight loss vs. temperature by thermogravimetric analysis (TGA) and effluent $NH_3$ and propene by mass spectrometry. The sample had a Brønsted acidity of 90.07 mmol/g, indicating that aluminum sites are incorporated into the framework of the molecular sieve.

The invention claimed is:

1. An organic nitrogen compound, wherein the organic nitrogen compound is a bromide salt or a hydroxide salt of a cation having the following structure (1):

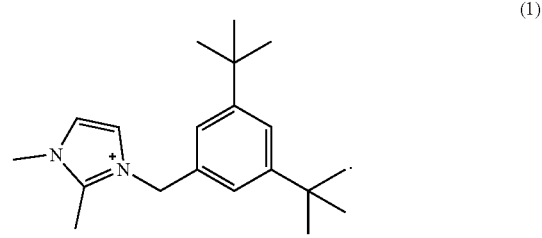 [SMILES: Cc1n(C)cc[n+]1Cc1cc(C(C)(C)C)cc(C(C)(C)C)c1]

(1)